(12) United States Patent
Dou et al.

(10) Patent No.: US 11,404,724 B2
(45) Date of Patent: Aug. 2, 2022

(54) ELECTROLYTE SOLUTION INCLUDING MULTI-CYANO COMPOUND ADDITIVE AND BATTERY INCLUDING THE SAME

(71) Applicant: CONTEMPORARY AMPEREX TECHNOLOGY CO., LIMITED, Ningde (CN)

(72) Inventors: Shushi Dou, Ningde (CN); Chunhua Hu, Ningde (CN); Tiancheng Yi, Ningde (CN); Jian Yan, Ningde (CN); Chengdu Liang, Ningde (CN); Li Hao, Ningde (CN)

(73) Assignee: CONTEMPORARY AMPEREX TECHNOLOGY CO., LIMITED, Ningde (CN)

( * ) Notice: Subject to any disclaimer, the term of this patent is extended or adjusted under 35 U.S.C. 154(b) by 166 days.

(21) Appl. No.: 16/624,192

(22) PCT Filed: Jul. 18, 2017

(86) PCT No.: PCT/CN2017/093310
§ 371 (c)(1),
(2) Date: Dec. 18, 2019

(87) PCT Pub. No.: WO2018/232807
PCT Pub. Date: Dec. 27, 2018

(65) Prior Publication Data
US 2020/0176817 A1  Jun. 4, 2020

(30) Foreign Application Priority Data

Jun. 21, 2017 (CN) .......................... 201710473970.7

(51) Int. Cl.
H01M 10/0567 (2010.01)
C07C 255/04 (2006.01)
H01M 10/0525 (2010.01)

(52) U.S. Cl.
CPC ....... *H01M 10/0567* (2013.01); *C07C 255/04* (2013.01); *H01M 10/0525* (2013.01); *H01M 2300/0025* (2013.01)

(58) Field of Classification Search
CPC .......... H01M 10/0567; H01M 10/0525; C07C 255/04
USPC ....................................................... 429/339
See application file for complete search history.

(56) References Cited

U.S. PATENT DOCUMENTS

2005/0256218 A1* 11/2005 Lachowicz ............... C08F 2/50
522/6
2008/0248397 A1  10/2008 Jung et al.
2012/0214058 A1*  8/2012 Kim ..................... H01M 4/661
429/207
2014/0322596 A1* 10/2014 Shatunov .......... H01M 10/0567
429/188
2015/0349381 A1  12/2015 Hwang
2016/0294007 A1  10/2016 Kefei
2016/0301103 A1  10/2016 Kim

FOREIGN PATENT DOCUMENTS

| CN | 104766995 A | 7/2015 |
|---|---|---|
| CN | 105074993 A | 11/2015 |
| CN | 105322223 A | 2/2016 |
| CN | 103208648 B | 12/2016 |
| EP | 2365571 A2 | 9/2011 |
| EP | 2796926 A2 | 10/2014 |
| JP | 2010073366 A | 4/2010 |

OTHER PUBLICATIONS

Odinets et al., Intramolecular Cyclization of ω-Haloalkylsubstituted Thiophosphorylacetonitriles: Synthesis and Stereochemistry of 3-Cyano-2-oxo-1,2-thiaphosphacyclanes, 2002, Heteroatom Chemistry, 13, 1-21 (Year: 2002).*
Bolte, M., 4-Acetyl-4-methylheptanedinitrile at 173 K, 1998, Acta crystallographica, C54, 1461-1462 (Year: 1998).*
Felton et al., Efficient electrocatalytic addition reactions of allyl phenyl sulfone to electron deficient alkenes, 2005, Tetrahedron, 61, 3515-3523 (Year: 2005).*

(Continued)

*Primary Examiner* — Sean P Cullen
(74) *Attorney, Agent, or Firm* — Tucker Ellis LLP

(57) ABSTRACT

The present application relates to the field of energy storage materials, and particularly, to an electrolytic solution and a battery using the electrolytic solution. The electrolytic solution of the present application contains an additive, the additive including a multi-cyano compound represented by formula (I). The multi-cyano compound of the present application has a stronger complexation with a transition metal on the surface of a positive electrode material, and therefore a protective film can be formed on the surface of the positive electrode material, and the dissolution of the transition metal is effectively suppressed; the surface activity of the positive electrode material is reduced, thereby suppressing side reactions, such as the decomposition of the electrolytic solution on the surface of the positive electrode material; and the cycle performance and storage performance of a battery under wide range of working voltage and wide range of operating temperature conditions are thus improved.

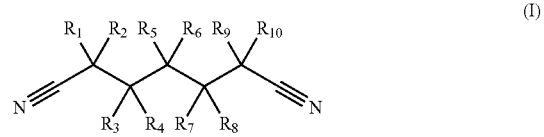

(I)

8 Claims, No Drawings

(56) References Cited

OTHER PUBLICATIONS

Bolte, M., 4-Benzoyl-4-(2-cyanoethyl)heptanedinitrile at 143 K, 1998, Acta crystallographica, C54, 852-854 (Year: 1998).*
Extended European Search Report for corresponding European Patent Application No. 17914380.5, dated May 29, 2020, 10 pages.
G.Y Kim et al.:"The Effect of Some Nitriles as Electrolyte additives in Li-Ion Batteries", Journal of the Electrochemical Society, vol. 162, No. 3, dated Jan. 3, 2015, pp. A437-A447, XP055557831, US.
International Search Report from corresponding International Patent Application No. PCT/CN2017/093310, dated Mar. 19, 2018, 4 pages.

\* cited by examiner

ELECTROLYTE SOLUTION INCLUDING MULTI-CYANO COMPOUND ADDITIVE AND BATTERY INCLUDING THE SAME

TECHNICAL FIELD

The present application relates to the field of energy storage materials, and in particular, to an electrolytic solution and a battery using the electrolytic solution.

BACKGROUND

Secondary batteries are widely used in electric vehicles and consumer electronic products due to their advantages of high energy density, high output power, long cycle life and small environmental pollution. The current demand on lithium-ion batteries still includes: high voltage, high power, long cycle life, long storage life and excellent safety performance.

Most of the current secondary batteries apply an electrolyte system, in which lithium hexafluorophosphate is used as conductive lithium salt and a cyclic carbonate and/or a chain carbonate is used as solvent. However, the above electrolyte system still has many deficiencies. For example, the cycle performance and storage performance of the above electrolyte system need to be improved under a condition of high voltage and high temperature.

The present application is made based on the above.

SUMMARY

In order to solve the above problems, the inventor conducted intensive researches and found that the multi-cyano compound of the present application has strong complexation with the transition metal on the surface of the positive electrode material. In this way, a protective film can be formed on the surface of the positive electrode material to effectively suppress dissolution of the transition metal; the positive electrode material has reduced surface activity and thus side reactions such as the decomposition of the electrolytic solution on the surface of the positive electrode material can be suppressed; and the battery has improved cycling performance and storage performance under a wide range of operating voltage and wide range of operating temperature condition. The present application is obtained based on the above.

An object of the present application is to provide an electrolytic solution. The electrolytic solution includes an additive, and the additive includes a multi-cyano compound represented by Formula I:

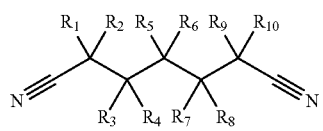

(I)

wherein $R_1$, $R_2$, $R_3$, $R_4$, $R_5$, $R_6$, $R_7$, $R_8$, $R_9$, and $R_{10}$ are each independently selected from the group consisting of a hydrogen atom, a substituted or unsubstituted $C_1$-$C_{12}$ alkyl, a substituted or unsubstituted $C_2$-$C_{12}$ alkenyl, a substituted or unsubstituted $C_2$-$C_{12}$ alkynyl, a substituted or unsubstituted $C_2$-$C_{12}$ cyano-containing group, a substituted or unsubstituted $C_2$-$C_{12}$ carbalkoxy, a substituted or unsubstituted $C_7$-$C_{22}$ aromatic ester group, a substituted or unsubstituted $C_2$-$C_{12}$ alkylcarbonyl, a substituted or unsubstituted $C_7$-$C_{22}$ arylcarbonyl, a substituted or unsubstituted $C_1$-$C_{12}$ alkylsulfonyl, a substituted or unsubstituted $C_6$-$C_{22}$ arylsulfonyl, and a substituted or unsubstituted $C_1$-$C_{12}$ alkyl thiophosphonate group;

at least one of $R_1$, $R_2$, $R_3$, $R_4$, $R_5$, $R_6$, $R_7$, $R_8$, $R_9$, and $R_{10}$ is a substituted or unsubstituted $C_7$-$C_{22}$ aromatic ester group, a substituted or unsubstituted $C_2$-$C_{12}$ alkylcarbonyl, a substituted or unsubstituted $C_7$-$C_{22}$ arylcarbonyl, a substituted or unsubstituted $C_1$-$C_{12}$ alkylsulfonyl, a substituted or unsubstituted $C_6$-$C_{22}$ arylsulfonyl, or a substituted or unsubstituted $C_1$-$C_{12}$ alkyl thiophosphate group; and the substituent, if present, is selected from the group consisting of halogen, cyano, $C_1$-$C_6$ alkyl, and combinations thereof.

Another object of the present application is to provide a secondary battery including a positive electrode plate, a negative electrode plate, a separator disposed between the positive electrode plate and the negative electrode plate, and the electrolytic solution of the present application.

The technical solutions of the present application has at least the following beneficial effects:

The multi-cyano compound of the present application has a strong complexation with the transition metal on the surface of the positive electrode material. In this way, a protective film can be formed on the surface of the positive electrode material to effectively suppress dissolution of the transition metal; the positive electrode material has reduced surface activity and thus side reactions such as the decomposition of the electrolytic solution on the surface of the positive electrode material can be suppressed; and the battery has improved cycling performance and storage performance under a wide range of operating voltage and wide range of operating temperature condition. The present application is obtained based on the above.

DESCRIPTION OF EMBODIMENTS

For clearly explaining the objects, technical solutions, and beneficial technical effects of the present application, the present application is described in detail with reference to the embodiments. It should be understood that the embodiments described in the present disclosure are merely illustrative, but not intended to limit the present application. The formulations, proportions, etc. described in the embodiments can be selected according to actual conditions without substantial influence on the results.

The electrolytic solution and the secondary battery according to the present application will be described in detail below.

The electrolytic solution according to a first aspect of the present application is first described.

In order to achieve the foregoing objects of the present application, a first aspect of the embodiments of the present application provides an electrolytic solution, and the electrolytic solution contains a multi-cyano compound represented by Formula I.

The electrolytic solution described herein may be a liquid electrolytic solution or a solid electrolytic solution. The liquid electrolytic solution is taken as an example to explain the present application. The electrolytic solution according to the embodiments of the present application includes an organic solvent, an electrolyte salt, and an additive. The additive includes the multi-cyano compound of the present application.

(Multi-Cyano Compounds)

The additive in the embodiments of the present application contains a multi-cyano compound, and the multi-cyano compound is at least one of the compounds represented by Formula I:

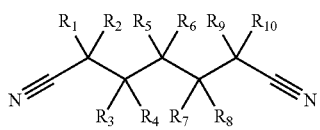
(I)

in which $R_1$, $R_2$, $R_3$, $R_4$, $R_5$, $R_6$, $R_7$, $R_8$, $R_9$, and $R_{10}$ are each independently selected from the group consisting of a hydrogen atom, a substituted or unsubstituted $C_1$-$C_{12}$ alkyl, a substituted or unsubstituted $C_2$-$C_{12}$ alkenyl, a substituted or unsubstituted $C_2$-$C_{12}$ alkynyl, a substituted or unsubstituted $C_2$-$C_{12}$ cyano-containing group, a substituted or unsubstituted $C_2$-$C_{12}$ carbalkoxy, a substituted or unsubstituted $C_7$-$C_{22}$ aromatic ester group, a substituted or unsubstituted $C_2$-$C_{12}$ alkylcarbonyl, a substituted or unsubstituted $C_7$-$C_{22}$ arylcarbonyl, a substituted or unsubstituted $C_1$-$C_{12}$ alkylsulfonyl, a substituted or unsubstituted $C_6$-$C_{22}$ arylsulfonyl, and a substituted or unsubstituted $C_1$-$C_{12}$ alkyl thiophosphate group;

at least one of $R_1$, $R_2$, $R_3$, $R_4$, $R_5$, $R_6$, $R_7$, $R_8$, $R_9$, and $R_{10}$ is a substituted or unsubstituted $C_7$-$C_{22}$ aromatic ester group, a substituted or unsubstituted $C_2$-$C_{12}$ alkylcarbonyl, a substituted or unsubstituted $C_7$-$C_{22}$ arylcarbonyl, a substituted or unsubstituted $C_1$-$C_{12}$ alkylsulfonyl, a substituted or unsubstituted $C_6$-$C_{22}$ arylsulfonyl, or a substituted or unsubstituted $C_1$-$C_{12}$ alkyl thiophosphate group; and the substituent, if present, is selected from the group consisting of halogen, cyano, $C_1$-$C_6$ alkyl, and combinations thereof.

Preferably, the substituent is fluorine, and some or all of hydrogen atoms of the above-mentioned groups may be substituted with a fluorine atom.

In the substituents above, the carbalkoxy refers to an ester group substituted with alkyl, i.e.,

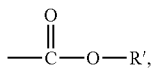

where R' is a substituted or unsubstituted alkyl; the aromatic ester group refers to an ester group substituted with aryl, i.e.,

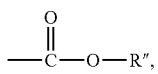

where R" is substituted or unsubstituted aryl; the alkylcarbonyl refers to alkyl-substituted carbonyl,

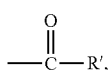

where R' is a substituted or unsubstituted alkyl; the arylcarbonyl refers to aryl-substituted carbonyl, i.e.,

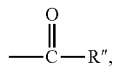

where R" is substituted or unsubstituted aryl; the alkylsulfonyl refers to alkyl-substituted sulfonyl, i.e.,

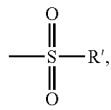

where R' is a substituted or unsubstituted alkyl; and the arylsulfonyl refers to aryl-substituted sulfonyl, i.e.,

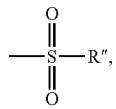

where R" is substituted or unsubstituted aryl; and the alkyl thiophosphonate group refers to an alkyl-substituted thiophosphonate group, i.e.,

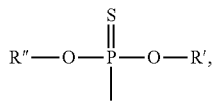

where R' and R" are a substituted or unsubstituted alkyl.

Among them, alkyl, alkenyl, and alkynyl may be chain substituents or cyclic substituents, and the chain substituents may be linear substituents or branched substituents.

The multi-cyano compound of the present application is added into the electrolytic solution as an additive. Due to at least two cyano groups, the multi-cyano compound can be stably adsorbed on the surface of the positive electrode material by means of a strong complexation effect between N atoms in the structure and transition metal atoms. In addition, the multi-cyano compound further contains C=O group, S=O group, and/or P=S group, which can also be complexed with metal elements on the surface of the positive electrode material, thereby increasing adsorption sites. In this way, the multi-cyano compound can be absorbed on the surface of the positive electrode material more stably. The multi-cyano compound can protect the surface of the positive electrode material and effectively suppress the dissolution of transition metals, while reducing the surface activity of the positive electrode material and in turn suppressing side reactions such as decomposition of the electrolytic solution on the surface of the positive electrode material. Therefore, the multi-cyano compound can improve the cycle performance and storage performance of the lithium ion battery, and increase the capacy retention rate of the battery under high temperature and high pressure conditions.

As an improvement of the electrolytic solution of the embodiments of the present application, when $R_1$, $R_2$, $R_3$, $R_4$, $R_7$, $R_8$, $R_9$, and $R_{10}$ are each a hydrogen atom, the multi-cyano compound is at least one of compounds presented by Formula I-1:

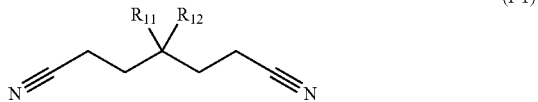
(I-1)

in which $R_{11}$ and $R_{12}$ are each independently selected from the group consisting of a hydrogen atom, a substituted or unsubstituted $C_1$-$C_8$ alkyl, a substituted or unsubstituted $C_2$-$C_8$ alkenyl, a substituted or unsubstituted $C_2$-$C_{12}$ alkynyl, a substituted or unsubstituted $C_2$-$C_8$ cyano-containing group, a substituted or unsubstituted $C_2$-$C_8$ carbalkoxy, a substituted or unsubstituted $C_7$-$C_{16}$ aromatic ester group, a substituted or unsubstituted $C_2$-$C_8$ alkylcarbonyl, a substituted or unsubstituted $C_7$-$C_{16}$ arylcarbonyl, a substituted or unsubstituted $C_1$-$C_8$ alkylsulfonyl, a substituted or unsubstituted $C_6$-$C_{16}$ arylsulfonyl, and a substituted or unsubstituted $C_1$-$C_8$ alkyl thiophosphate group;

at least one of $R_{11}$ and $R_{12}$ is a substituted or unsubstituted $C_7$-$C_{16}$ aromatic ester group, a substituted or unsubstituted $C_2$-$C_8$ alkylcarbonyl, a substituted or unsubstituted $C_7$-$C_{16}$ arylcarbonyl, a substituted or unsubstituted $C_1$-$C_8$ alkylsulfonyl, a substituted or unsubstituted $C_6$-$C_{16}$ arylsulfonyl, or a substituted or unsubstituted $C_1$-$C_8$ alkyl thiophosphate group; and the substituent, if present, is selected from the group consisting of halogen, cyano, $C_1$-$C_6$ alkyl, and combinations thereof.

Among them, alkyl, alkenyl, and alkynyl may be chain substituents or cyclic substituents, and the chain substituents may be linear substituents or branched substituents.

Further preferably, at least one of $R_{11}$ and $R_{12}$ is a substituted or unsubstituted $C_7$-$C_{12}$ aromatic ester group, a substituted or unsubstituted $C_2$-$C_6$ alkylcarbonyl, a substituted or unsubstituted $C_7$-$C_{12}$ arylcarbonyl, a substituted or unsubstituted $C_1$-$C_6$ alkylsulfonyl, a substituted or unsubstituted $C_6$-$C_{12}$ arylsulfonyl, or a substituted or unsubstituted $C_1$-$C_6$ alkyl thiophosphate group.

As an improvement of the electrolytic solution of the embodiments of the present application, when $R_3$, $R_4$, $R_5$, $R_6$, $R_7$, and $R_8$ are each a hydrogen atom, the multi-cyano compound is at least one of compounds represented by Formula I-2:

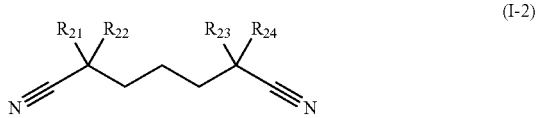
(I-2)

in which $R_{21}$, $R_{22}$, $R_{23}$, and $R_{24}$ are each independently selected from the group consisting of a hydrogen atom, a substituted or unsubstituted $C_1$-$C_8$ alkyl, a substituted or unsubstituted $C_2$-$C_8$ alkenyl, a substituted or unsubstituted $C_2$-$C_{12}$ alkynyl, a substituted or unsubstituted $C_2$-$C_8$ cyano-containing group, a substituted or unsubstituted $C_2$-$C_8$ carbalkoxy, a substituted or unsubstituted $C_7$-$C_{16}$ aromatic ester group, a substituted or unsubstituted $C_2$-$C_8$ alkylcarbonyl, a substituted or unsubstituted $C_7$-$C_{16}$ arylcarbonyl, a substituted or unsubstituted $C_1$-$C_8$ alkylsulfonyl, a substituted or unsubstituted $C_6$-$C_{16}$ arylsulfonyl, and a substituted or unsubstituted $C_1$-$C_8$ alkyl thiophosphate group;

at least one of $R_{21}$, $R_{22}$, $R_{23}$, and $R_{24}$ is a substituted or unsubstituted $C_7$-$C_{16}$ aromatic ester group, a substituted or unsubstituted $C_2$-$C_8$ alkylcarbonyl, a substituted or unsubstituted $C_7$-$C_{16}$ arylcarbonyl, a substituted or unsubstituted $C_1$-$C_8$ alkylsulfonyl, a substituted or unsubstituted $C_6$-$C_{16}$ arylsulfonyl, or a substituted or unsubstituted $C_1$-$C_8$ alkyl thiophosphate group; and the substituent, if present, is selected from the group consisting of halogen, cyano, $C_1$-$C_6$ alkyl, and combinations thereof.

Among them, alkyl, alkenyl, and alkynyl may be chain substituents or cyclic substituents, and the chain substituents may be linear substituents or branched substituents.

As an improvement of the electrolytic solution of the embodiments of the present application, the compounds represented by Formula I-2 may be the compounds represented by Formula I-2a:

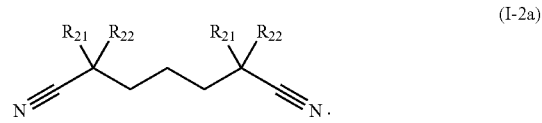
(I-2a)

The multi-cyano compounds having a symmetrical structure are easy to be synthesized, and the adsorption sites are also symmetrical, such that the multi-cyano compounds can be more stably absorbed on the surface of the positive electrode material.

As an improvement of the electrolytic solution of the embodiments of the present application, the multi-cyano compound is at least one of the following compounds:

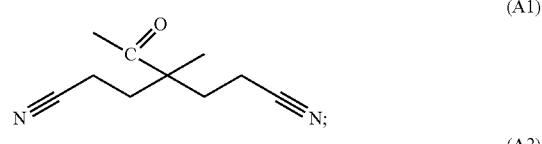
(A1)

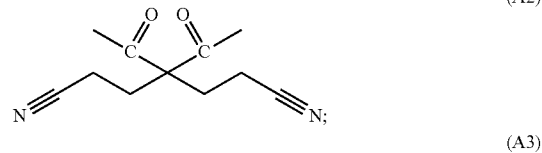
(A2)

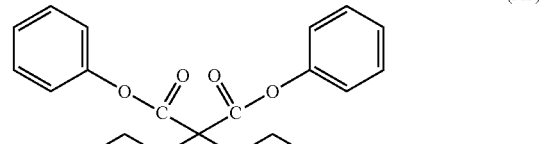
(A3)

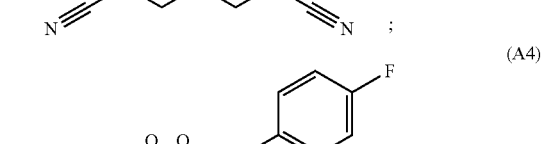
(A4)

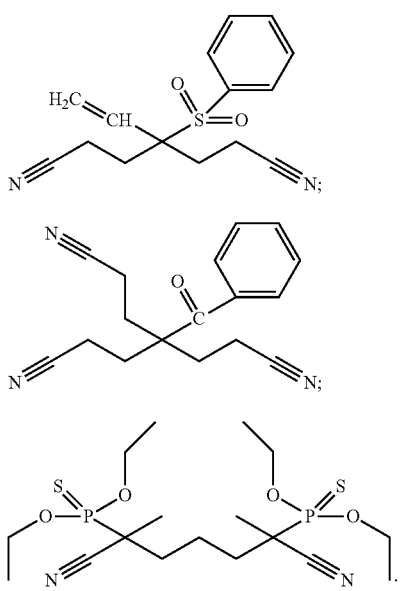

(A5)

(A6)

(A7)

As an improvement of the electrolytic solution of the embodiments of the present application, the multi-cyano compound is at least one of the following compounds and combinations thereof, but is not limited thereto:

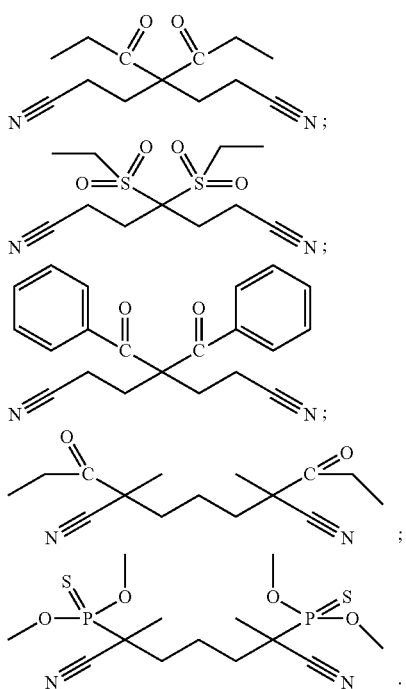

As an improvement of the electrolytic solution of the embodiments of the present application, a mass percentage of the multi-cyano compound in the electrolytic solution is 0.01% to 10%, preferably 0.1% to 3.5%. If the concentration of the multi-cyano compound in the electrolytic solution is too low, the complexation adsorption of the multi-cyano compound on the surface of the positive electrode material will be too sparse to effectively suppress the side reactions such as the decomposition of the electrolytic solution. If the concentration of the multi-cyano compound in the electrolytic solution is too high, the complexation adsorption of the multi-cyano compound on the surface of the positive electrode material will be too dense, thereby resulting in an increase in the resistance of the battery and negatively affecting the cycle performance and rate performance of the battery. An upper limit of a range of the mass percentage of the multi-cyano compound in the electrolytic solution may be arbitrarily selected from 10%, 9%, 8%, 7%, 6%, 5%, 4.5%, 4%, 3.5%, 3%, 2%, 1%, or 0.8%, and a lower limit thereof may be arbitrarily selected from 0.001%, 0.005%, 0.01%, 0.05%, 0.1%, 0.3%, 0.5%, or 0.6%. Further preferably, the mass percentage of the multi-cyano compound in the electrolytic solution is 0.1% to 3.5%.

(Additive A)

Another additive, as additive A, may be added into the electrolytic solution of the present application, and the additive A is, for example, any one of the following compounds (a) to (o).

(a) Unsaturated Cyclic Carbonate Compounds

The unsaturated cyclic carbonate compound is selected from a group consisting of compounds represented by Formula II-0 and combinations thereof;

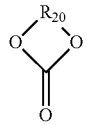

(II-0)

in which $R_{20}$ is selected from the group consisting of an alkenyl-substituted $C_1$-$C_6$ alkylene, and a substituted or unsubstituted $C_2$-$C_6$ alkenylene.

The unsaturated cyclic carbonate compound is at least one of the compounds having the following specific structures:

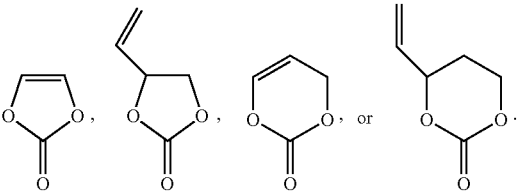

(b) Halogenated Cyclic Carbonate Compound

The halogenated cyclic carbonate compound is at least one of compounds represented by Formula II-1:

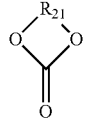

(II-1)

in which $R_{21}$ is selected from the group consisting of a halogenated $C_1$-$C_6$ alkylene, and a halogenated $C_2$-$C_6$ alkenylene.

The halogenated cyclic carbonate compound is selected from the group consisting of fluoroethylene carbonate (FEC), fluoropropylene carbonate (FPC), trifluoropropylene carbonate (TFPC).

(c) Sulfate Compounds

The sulfate compound is preferably a cyclic sulfate compound, and the cyclic sulfate compound is at least one of the compounds represented by Formula II-2;

(II-2)

in which $R_{22}$ is selected from the group consisting of a substituted or unsubstituted $C_1$-$C_6$ alkyllene, and a substituted or unsubstituted $C_2$-$C_6$ alkenylene; and the substituent, if present, is selected from the group consisting of halogen, $C_1$-$C_3$ alkyl, and $C_2$-$C_4$ alkenyl.

Further preferably, $R_{22}$ is selected from the group consisting of a substituted or unsubstituted $C_1$-$C_4$ alkylene, and a substituted or unsubstituted $C_2$-$C_4$ alkenylene; and the substituent, if present, is selected from the group consisting of halogen, $C_1$-$C_3$ alkyl, and $C_2$-$C_4$ alkenyl.

The cyclic sulfate compound is selected from the group consisting of 1,3,2-dioxathiolane 2,2-dioxide (DTD), trimethylene sulfate (TMS), 4-methyl-2,2-dioxo-1,3,2-dioxathiolane (PLS), having the following structures:

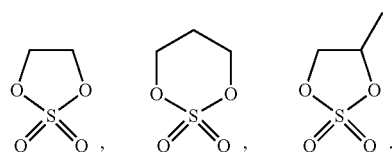

As an improvement of the electrolytic solution of the embodiments of the present application, the cyclic sulfate compound may be further selected from:

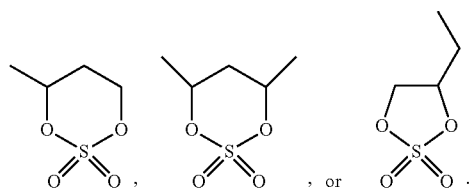

(d) Sultone Compounds

The sultone compound is at least one of compounds represented by Formula II-3:

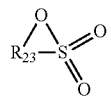
(II-3)

in which $R_{23}$ is selected from the group consisting of a substituted or unsubstituted $C_1$-$C_6$ alkylene, and a substituted or unsubstituted $C_2$-$C_6$ alkenylene; and the substituent, if present, is selected from the group consisting of halogen, $C_1$-$C_3$ alkyl, and $C_2$-$C_4$ alkenyl.

Specifically, the sultone compound is selected from the group consisting of 1,3-propane sultone (PS), prop-1-ene-1,3-sultone (PES), having the following specific structures:

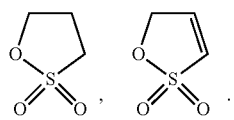

The sultone compound may be further selected from:

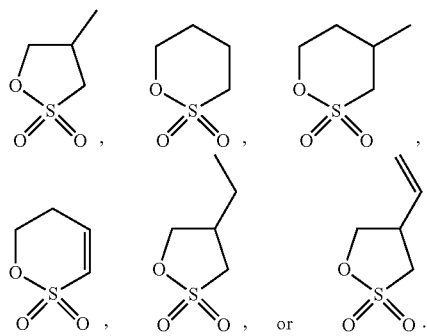

(e) Disulfate Compounds

The disulfate compound is a compound containing two sulfate groups, and preferably, is a methylene disulfonate compound. Specifically, the disulfate compound may be at least one of the compounds represented by Formula II-4:

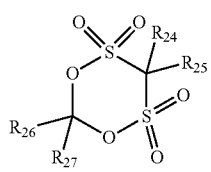
(II-4)

in which $R_{24}$, $R_{25}$, $R_{26}$, and $R_{27}$ are each independently selected from the group consisting of hydrogen, halogen, a substituted or unsubstituted $C_1$-$C_{10}$ alkyl, and a substituted or unsubstituted $C_2$-$C_{10}$ alkenyl; and the substituent, if present, is selected from the group consisting of halogen, $C_1$-$C_3$ alkyl, and $C_2$-$C_4$ alkenyl.

The methylene disulfonate compound is methylene methanedisulfonate (abbreviated as MMDS);

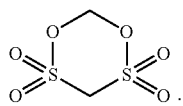

The methylene disulfonate compound may be further selected from the group consisting of 3-methyl-methylene methanedisulfonate, which have any one of the following structures:

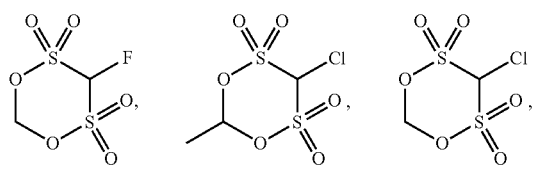

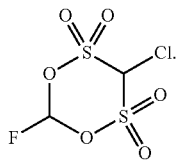

(f) Sulfite Compounds

The sulfite compound is preferably a cyclic sulfite compound, and specifically, may be at least one of the compounds represented by Formula II-5:

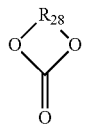

(II-5)

in which $R_{28}$ is selected from the group consisting of a substituted or unsubstituted $C_1$-$C_6$ alkylene, and a substituted or unsubstituted $C_2$-$C_6$ alkenylene; and the substituent, if present, is selected from the group consisting of halogen, $C_1$-$C_3$ alkyl, and $C_2$-$C_4$ alkenyl.

The sulfite compound may be selected from the group consisting of ethylene sulfite (abbreviated as ES), propylene sulfite (abbreviated as PS), and butane sulfite (abbreviated as BS).

(g) Nitrile Compounds

The nitrile compound may be selected from the group consisting of acetonitrile, propionitrile, succinonitrile, glutaronitrile, hexanedinitrile, heptanedinitrile, octanedinitrile, decanedinitrile, and combinations thereof.

More preferably, the nitrile compound may be selected from the group consisting of succinonitrile, glutaronitrile, hexanedinitrile, heptanedinitrile, and combinations thereof.

(h) Aromatic Compounds

The aromatic compound may be selected from the group consisting of an aromatic compound having branched alkyl, such as cyclohexylbenzene, fluorocyclohexylbenzene (1-fluoro-2-cyclohexylbenzene, 1-fluoro-3-cyclohexylbenzene, 1-fluoro-4-cyclohexylbenzene), tert-butylbenzene, tert-amylbenzene, 1-fluoro-4-tert-butylbenzene, etc., and other aromatic compounds, such as biphenyl, terphenyl (ortho, meta, para), diphenyl ether, fluorobenzene, difluorobenzene (ortho, meta, para), anisole, 2,4-difluoroanisole, partially hydrogenated terphenyl (1,2-dicyclohexylbenzene, 2-phenyldicyclohexyl, 1,2-diphenylcyclohexane, o-cyclohexyl biphenyl), etc.

Among them, one or two or more of biphenyl, terphenyl (ortho, meta, para), fluorobenzene, cyclohexylbenzene, tert-butylbenzene and tert-amylbenzene, particularly one or two or more of biphenyl, o-terphenyl, fluorobenzene, cyclohexylbenzene, or tert-amylbenzene are selected.

(i) Isocyanate Compounds

The isocyanate compounds may be selected from the group consisting of methyl isocyanate, ethyl isocyanate, butyl isocyanate, phenyl isocyanate, tetramethylene diisocyanate, hexamethylene diisocyanate, octamethylene diisocyanate, 1,4-phenylene diisocyanate, 2-isocyanatoethyl crylate, 2-isocyanatoethyl methacrylate, and combinations thereof.

Among them, one or two or more of hexamethylene diisocyanate, octamethylene diisocyanate, 2-isocyanatoethyl crylate, and 2-isocyanatoethyl methacrylate are preferably selected.

(j) Phosphazene Compounds

The phosphazene compound may be, for example, a cyclic phosphazene compound such as methoxy pentafluorocyclotriphosphazene, ethoxy pentafluorocyclotriphosphazene, phenoxy pentafluorocyclotriphosphazene, ethoxy heptafluorocyclotetraphosphazene, or the like.

Among them, methoxy pentafluorocyclotriphosphazene, ethoxy pentafluorocyclotriphosphazene, or phenoxy pentafluorocyclotriphosphazene is preferable, and methoxy pentafluorocyclotriphosphazene or ethoxy pentafluorocyclotriphosphazene is more preferably selected.

(k) Cyclic Anhydride Compounds

Suitable examples of the cyclic anhydride compound may include chain carboxylic anhydrides such as acetic anhydride, propionic anhydride, etc., or cyclic anhydrides such as succinic anhydride, maleic anhydride, 2-allyl succinic anhydride, glutaric anhydride, itaconic anhydride, 3-sulfo-propionic anhydride, and the like.

Among them, succinic anhydride, maleic anhydride, and 2-allyl succinic anhydride are preferable, and succinic anhydride and 2-allyl succinic anhydride are more preferable.

(l) Phosphite Compound

The phosphite compound may be a silane phosphite compound, and particularly, at least one of the compounds represented by Formula II-6:

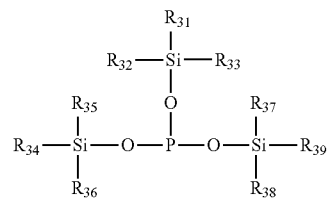

(II-6)

in which $R_{31}$, $R_{32}$, $R_{33}$, $R_{34}$, $R_{35}$, $R_{36}$, $R_{37}$, $R_{38}$, and $R_{39}$ are each a substituted or unsubstituted $C_1$-$C_6$ alkyl; and the substituent, if present, is halogen.

The silane phosphite compounds may be at least one of the following compounds:

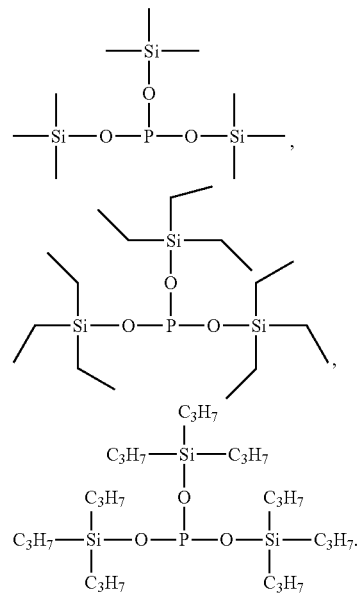

(m) Phosphate Compounds

The phosphate compound may be a silane phosphate compound, and particularly, at least one of the compounds represented by Formula II-7:

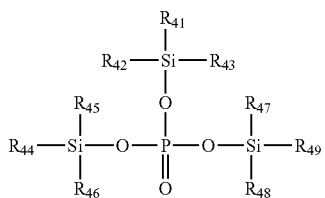
(II-7)

in which $R_{41}$, $R_{42}$, $R_{43}$, $R_{44}$, $R_{45}$, $R_{46}$, $R_{47}$, $R_{48}$, and $R_{49}$ are each a substituted or unsubstituted $C_1$-$C_6$ alkyl; and the substituent, if present, is a halogen atome.

The silane phosphate compounds may be at least one of the following compounds:

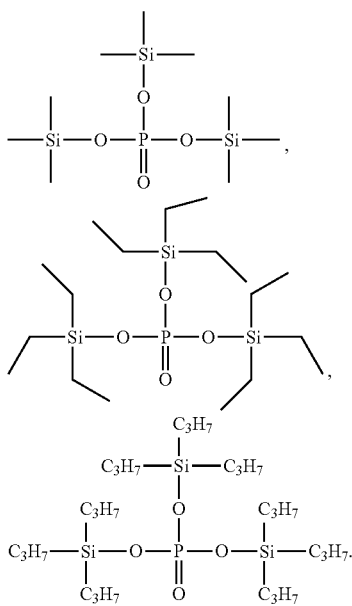

(n) Borate Ester Compounds

The borate ester compound may be a silane borate ester compound, and particularly, at least one of the compounds represented by II-8:

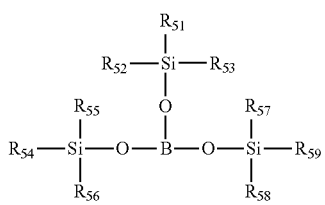
(II-8)

in which $R_{51}$, $R_{52}$, $R_{53}$, $R_{54}$, $R_{55}$, $R_{56}$, $R_{57}$, $R_{58}$, and $R_{59}$ are each a substituted or unsubstituted $C_1$-$C_6$ alkyl; and the substituent, if present, is halogen.

The silane borate ester compound may be at least one of the following compounds:

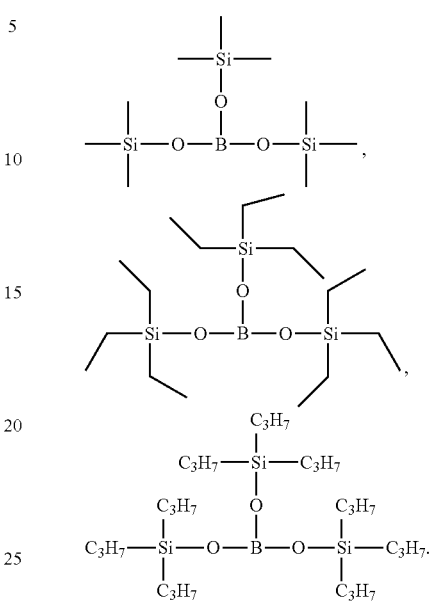

(o) Carboxylate Ester

The carboxylate ester may be a chain carboxylate or a cyclic carboxylate. The chain carboxylate and cyclic carboxylate may contain unsaturated bond or a halogen atom.

One or more of ethyl acetate (abbreviated as EA), methyl butyrate (abbreviated as MB), ethyl butyrate (abbreviated as EB), trifluoroethyl acetate (abbreviated as TFEA), trifluoroethyl acetate (abbreviated as ETFA), or methyl pentafluoropropionate (abbreviated as MPFP) are preferable.

As an improvement of the electrolytic solution of the embodiments of the present application, a mass percentage of the additive A in the electrolytic solution is 0.01% to 30%.

In the Formula I, the Formula I-1 or the Formula I-2:

$C_1$-$C_{12}$ alkyl is alkyl having 1 to 12 carbon atoms, and can be a chain alkyl or a cycloalkyl; hydrogen on a ring of cycloalkyl can be substituted by alkyl; a preferable lower limit of a number of carbon atoms of alkyl is 1, 2, 3, 4, or 5; and a preferable upper limit of the number of carbon atoms of alkyl is 3, 4, 5, 6, 8, 9, 10, or 12. Preferably, alkyl is having 1-10 carbon atoms is selected; more preferably, a chain alkyl having 1-6 carbon atoms or a cycloalkyl having 3-8 carbon atoms is selected; and most preferably, a chain alkyl having 1-4 carbon atoms or a cycloalkyl having 5-7 carbon atoms is selected. Examples of alkyl include: methyl, ethyl, n-propyl, iso-propyl, n-butyl, iso-butyl, sec-butyl, tert-butyl, n-amyl, iso-amyl, neo-amyl, hexyl, 2-methyl-amyl, 3-methyl-amyl, 1,1,2-trimethylpropyl, 3,3,-dimethyl-butyl, heptyl, 2-heptyl, 3-heptyl, 2-methylhexyl, 3-methylhexyl, iso-heptyl, octyl, nonyl, and decyl.

When the alkyl having 1 to 12 carbon atoms contains an ester group, a carbonyl group, a sulfonyl group, or a thiophosphate group, $C_2$-$C_{12}$ carbalkoxy, $C_2$-$C_{12}$ alkylcarbonyl, $C_2$-$C_{12}$ alkylsulfonyl, or $C_2$-$C_{12}$ alkyl thiophosphate group is obtained.

$C_2$-$C_{12}$ alkenyl is alkenyl having 2-12 carbon atoms, and can be a cyclic alkenyl or a chain alkenyl. The alkenyl preferably contains only one double-bond. A preferable lower limit of a number of carbon atoms of alkenyl is 3, 4, or 5, and a preferable upper limit thereof is 3, 4, 5, 6, 8, 9, 10, or 12. Preferably, alkenyl containing 2-10 carbon atoms is selected; and more preferably, alkenyl containing 2-6 carbon atoms is selected. Examples of the alkenyl include: vinyl, allyl, isopropenyl, pentenyl, cyclohexenyl, cyclohep-tenyl, and cyclooctenyl.

$C_2$-$C_{12}$ alkynyl is alkynyl having 2-12 atoms, and can be a cyclic alkynyl or a chain alkynyl. Alkynyl preferably contains only one triple bond. A preferable lower limit of a number of carbon atoms of alkynyl is 3, 4, or 5, and a preferable upper limit thereof is 3, 4, 5, 6, 8, 10, or 12. Preferably, alkynyl containing 2-10 carbon atoms is selected; more preferably, alkynyl containing 2-6 carbon atoms; and most preferably, alkynyl containing 2-5 carbon atoms is selected. Examples of the alkenyl include: acetenyl, propargyl, isopropynyl, pentynyl.

$C_6$-$C_{26}$ aryl contains an ester group, a carbonyl group, or a sulfonyl group, a $C_7$-$C_{22}$ aromatic ester group, a $C_7$-$C_{22}$ arylcarbonyl group, or a $C_6$-$C_{22}$ arylsulfonyl group is obtained. The $C_6$-$C_{26}$ aryl may be selected from phenyl, phenylalkyl, aryl containing at least one phenyl such as biphenyl, and polycyclic aryl such as naphthyl, anthryl, and phenanthryl; the biphenyl and the polycyclic aryl can be substituted by alkyl or alkenyl. Preferably, aryl having 6-18 carbon atoms is selected; more preferably, aryl containing 6-14 carbon atoms is selected; and most preferably, an aryl containing 6-9 carbon atoms is selected. Examples of the aryl include: phenyl, benzyl, biphenyl, p-tolyl, o-tolyl, m-tolyl.

The halogen is selected from fluorine, chlorine, or bromine, and fluorine is preferable.

In the general Formula II-0 to Formula II-8 in the embodiments of the present application:

$C_1$-$C_6$ alkylene is a linear or branched alkylene having 1-6 carbon atoms; a preferable lower limit of a number of carbon atoms of alkylene is 2 or 3, and a preferable upper limit thereof is 4, 5, or 6. Preferably, alkylene having 1-4 carbon atoms is selected. Specific examples of the alkyl group include methylene, ethylidene, propylidene, isopropylidene, butylidene, isobutylidene, sec-butylidene, pentylidene, and hexylidene.

$C_2$-$C_6$ alkenylene is a linear or branched alkenylene having 2-6 carbon atoms, and preferably contains only one double bond. A preferable lower limit of a number of carbon atoms of alkenylene is 3 or 4, and a preferable upper limit thereof is 3, 4, 5, or 6. Preferably, alkenylene containing 2-5 carbon atoms is selected. Examples of the alkenylene include: vinylidene, propylidene, isopropylidene, butenylidene, and pentenylidene.

The halogen is selected from fluorine, chlorine, or bromine, and fluorine is preferable.

(Organic Solvent)

The organic solvent used in the non-aqueous electrolytic solution of the present application may be preferably selected from the group consisting of cyclic carbonate, chain ester, lactone, ether, amide, and combinations thereof. In order to further improve the cycle performance at high temperature and high voltage and the storage performance at high temperature, the electrolyte preferably contains cyclic carbonate and chain carbonate.

The term "chain ester" used herein is a concept including both chain carbonate and chain carboxylic acid ester.

Examples of the cyclic carbonate include one or two or more selected from cyclic carbonates having carbon-carbon unsaturated bond, such as ethylene carbonate (abbreviated as EC), propylene carbonate (abbreviated as PC), 1,2-buty-lene carbonate, 2,3-butylene carbonate, vinylene carbonate (abbreviated as VC), vinyl ethylene carbonate (abbreviated as VEC), 4-ethynyl-1,3-dioxolan-2-one (abbreviated as EEC), and the like, and cyclic carbonates having fluorine atom, such as 4-fluoro-1,3-dioxolan-2-one (referred to as FEC), trans or cis-4,5-difluoro-1,3-dioxolan-2-one (referred to as DFEC), or the like, and more preferably, one or two or more selected from ethylene carbonate, propylene carbonate, 4-fluoro-1,3-dioxolan-2-one, vinylene carbonate, or 4-ethynyl-1,3-dioxolan-2-one (abbreviated as EEC).

Examples of the chain ester include: asymmetric chain carbonate, such as ethyl methyl carbonate (abbreviated as MEC), methyl propyl carbonate (abbreviated as MPC), methyl isopropyl carbonate (abbreviated as MIPC), methyl butyl carbonate, and ethyl propyl carbonate; symmetrical chain carbonate, such as dimethyl carbonate (abbreviated as DMC), diethyl carbonate (abbreviated as DEC), dipropyl carbonate, and dibutyl carbonate; and chain carboxylic acid ester, such as neovalerates (methyl neovalerate, ethyl neovalerate, propyl pivalate, etc.), methyl propionate, ethyl propionate, methyl acetate, and ethyl acetate.

Other suitable examples of the organic solvent may include: cyclic ester, such as tetrahydrofuran, 2-methyl tetrahydrofuran, 1, 4-dioxane, etc.; chain ester, such as 1, 2-dimethoxyethane, 1, 2-diethoxyethane, 1, 2-dibutoxy-ethane, etc.; amide, such as dimethylformamide; sulfone such as sulfolane; and lactones such as γ-butyrolactone, γ-valerolactone, and α-angelica lactone.

(Electrolyte Salt)

The following lithium slats are suitable examples of the salt for electrolyte of the present disclosure.

(Li Salts-Type 1)

Suitable examples are complex salts of "Lewis Acid and LiF", such as $LiPF_6$, $LiBF_4$, $LiAsF_6$, $LiSbF_6$, $LiPF_4(CF_3)_2$, $LiPF_3(C_2F_5)_3$, $LiPF_3(CF_3)_3$, $LiPF_3(iso-C_3F_7)_3$, and $LiPF_5(iso-C_3F_7)$. Preferable examples are $LiPF_6$, $LiBF_4$, and $LiAsF_6$. More preferable examples are $LiPF_6$ and $LiBF_4$.

(Li Salts-Type 2)

Suitable examples are "lithium imide salts or methylated lithium salts", such as $LiN(SO_2F)_2$, $LiN(SO_2CF_3)_2$, $LiN(SO_2C_2F_5)_2$, $(CF_2)_2(SO_2)_2NLi$ (cyclic), $(CF_2)_3(SO_2)_2NLi$ (cyclic), and $LiC(SO_2CF_3)_3$. Preferable examples are $LiN(SO_2F)_2$, $LiN(SO_2CF_3)_2$, and $LiN(SO_2C_2F_5)_2$. More preferable examples are $LiN(SO_2F)_2$ and $LiN(SO_2CF_3)_2$.

(Li Salts-Type 3)

Suitable examples are "lithium salts containing a $S(=O)_2O$ structure", such as $LiSO_3F$, $LiCF_3SO_3$, $CH_3SO_4Li$, $C_2H_5SO_4Li$, $C_3H_7SO_4Li$, lithium trifluoro (methanesulfonyloxy) borate (LiTFMSB), and lithium pentafluoro (methanesulfonyloxy) phosphate (LiPFMSP). Preferable examples are $LiSO_3F$, $CH_3SO_4Li$, $C_2H_5SO_4Li$, and LiTFMSB.

(Li Salts-Type 4)

Suitable examples are "lithium salts containing P=O or Cl=O", such as $LiPO_2F_2$, $Li_2PO_3F$, and $LiClO_4$. Preferable examples are $LiPO_2F_2$ and $Li_2PO_3F$.

(Li Slats-Type 5)

Suitable examples are "lithium salts with oxalate ligands as anions", such as lithium bis[oxalate-O,O'] borate (LiBOB), lithium difluoro[oxlate-O,O'] borate, lithium difluorobis[oxlate-O,O'] phosphate (LiPFO), and lithium tetrafluoro[oxalate-O,O'] phosphate. Preferable examples are LiBOB and LiPFO. One or more of these lithium salts can be used in the electrolyte.

The lithium salt is preferably selected from the group consisting of $LiPF_6$, $LiPO_2F_2$, $Li_2PO_3F$, $LiBF_4$, $LiSO_3F$, lithium trifluoro((methanesulfonyloxy) borate (LiTFMSB), $LiN(SO_2F)_2$, $LiN(SO_2CF_3)_2$, $LiN(SO_2C_2F_5)_2$, lithium bis[oxalate-O,O'] borate (LiBOB), lithium difluorobis[oxalate- O,O'] phosphate (LiPFO), lithium tetrafluoro[oxalte-O,O'] phosphate, and combinations thereof; more preferably, selected from the group consisting of LiPF$_6$, LiBF$_4$, LiSO$_3$F, lithium trifluoro((methanesulfonyloxy) borate (LiTFMSB), LiPO$_2$F$_2$, LiN(SO$_2$CF$_3$)$_2$, LiN(SO$_2$F)$_2$, lithium bis[oxalate-O,O'] borate (LiBOB), lithium difluorobis[oxalate-O,O'] phosphate (LiPFO), and combinations thereof; and most preferably, is LiPF$_6$.

(Preparation of Electrolytic Solution)

The electrolytic solution of the embodiments of the present application can be obtained, for example, by mixing the organic solvent, adding an electrolytic solution salt and the multi-cyano compound of the present application, and optionally adding at least one of the additives A described above.

(Synthesis of Multi-cyano Compounds)

(I) Preparation of compounds represented by Formula I-1:
The reaction equation is shown as below:

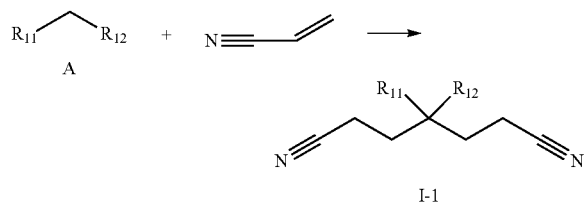

The specific steps of the preparation are as follow:

A precursor material A was mixed with acrylonitrile and stirred at room temperature for 16-20 hours. After the reaction was completed, distilled water was added, and the solid was filtered and dried to obtain the compound represented by the Formula I-1, with a yield of about 83%.

(II) Preparation of compounds represented by Formula I-2a:
The reaction equation is shown as below:

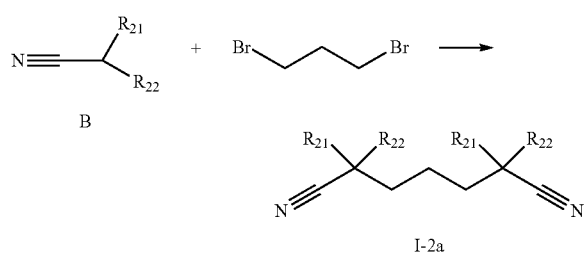

The specific steps of the preparation are as follow:

Under nitrogen protection, at −78° C., a precursor substance B and 1,3-dibromopropane were mixed and dissolved in a tetrahydrofuran solvent, and lithium diisopropylamide (LDA) was added. The temperature was maintained for 60 minutes, and 1.2 to 1.5 times equivalent of 1,3-dibromopropane in tetrahydrofuran solution was added to the system, and reacted for 16-20 hours after the temperature was slowly raised to 15-20° C., following by cooling to −10° C. Then the reaction was quenched by adding water, and then extracted, washed, dried, and spin-dried to obtain the compound represented by Formula I-2a, with a yield of about 90%.

The battery according to a second aspect of the embodiments of the present application is described below.

The battery according to the embodiments of the present application includes a positive electrode plate, a negative electrode plate, a separator disposed between the positive electrode plate and the negative electrode plate, and an electrolytic solution. It should be noted that the battery according to the embodiments of the present application may be a lithium ion battery, a sodium ion battery, or a magnesium ion battery.

When the battery is a lithium ion battery, the positive electrode includes a positive electrode active material capable of de-intercalating and intercalating lithium ions, and the negative electrode plate thereof includes a negative electrode active material capable of intercalating and de-intercalating lithium ions.

Specifically, when the battery is a lithium ion battery, the positive electrode active material can be selected from the group consisting of lithium cobalt oxide, lithium nickel oxide, lithium manganese oxide, lithium nickel manganese oxide, lithium nickel cobalt manganese oxide, lithium nickel cobalt aluminum oxide, a compound formed by doping a transition metal or a non-transition metal into the lithium transition metal oxides, and combinations thereof. The positive electrode active material can be a layered lithium-containing oxide, a spinel-type lithium-containing oxide, an olivine-type lithium-containing phosphate compound or the like. However, the positive electrode active material is not limited to the above materials. Any conventional material that can be used as a positive electrode active material of a lithium-ion battery can be adopted. These positive electrode active materials can be used individually or in combination.

Specifically, when the battery is a lithium ion battery, the negative electrode active material may be soft carbon, hard carbon, artificial graphite, natural graphite, silicon, silicon oxide, silicon carbon composite, lithium titanate, metal capable of forming an alloy with lithium, or the like. Specifically, a carbon-based negative electrode, a silicon-based negative electrode, a tin-based negative electrode, or the like can be used. However, the negative electrode active material is not limited to these materials. Any conventional material that can be used as a negative electrode active material of a lithium-ion battery can be adopted. These negative electrode active materials can be used individually or in combination.

When the battery is a sodium ion battery, the positive electrode includes a positive electrode active material capable of de-intercalating and intercalating sodium ions, and the negative electrode includes a negative electrode active material capable of de-intercalating and intercalating sodium ions. For example, the positive electrode active material may be sodium iron composite oxide (NaFeO$_2$), sodium cobalt composite oxide (NaCoO$_2$), sodium chromium complex oxide (NaCrO$_2$), sodium manganese composite oxide (NaMnO$_2$), sodium nickel composite oxide (NaNiO$_2$), sodium-nickel-titanium composite oxide (NaNi$_{1/2}$Ti$_{1/2}$O$_2$), sodium-nickel-manganese composite oxide (NaNi$_{1/2}$Mn$_{1/2}$O$_2$), sodium-iron-manganese composite oxide (Na$_{2/3}$Fe$_{1/3}$Mn$_{2/3}$O$_2$), sodium-nickel-cobalt-manganese composite oxide (NaNi$_{1/3}$Co$_{1/3}$Mn$_{1/3}$O$_2$), sodium iron phosphate compound (NaFePO$_4$), sodium manganese phosphate compound (NaMnPO$_4$), sodium cobalt phosphate compound (NaCoPO$_4$), etc. However, the positive electrode active material is not limited to the above materials. Any conventional material that can be used as a positive electrode active material of a sodium-ion battery can be adopted. These positive electrode active materials can be used individually or in combination.

The negative electrode active material may be carbon materials, such as hard carbon, natural graphite, artificial graphite, soft carbon, carbon black, acetylene black, carbon nanotubes, graphene, carbon nanofibers, and the like. In addition, examples of other negative electrode active materials include elemental substances of elements that alloy with sodium, such as Si, Ge, Pb, In, Zn, H, Ca, Sr, Ba, Ru, and Rh, and oxides and carbides containing these elements. However, the negative electrode active material is not limited to the above materials. Any conventional material that can be used as a negative electrode active material of a sodium-ion battery can be adopted. These positive electrode active materials can be used individually or in combination.

When the battery is a magnesium ion battery, the positive electrode includes a positive electrode active material capable of de-intercalating and intercalating magnesium ions, and the negative electrode includes a negative electrode active material capable of de-intercalating and intercalating magnesium ions. For example, the positive electrode active material may be $V_2O_5$, $MoO_3$, $MnO_2$, $TiS_2$, $MoS_2$, or the like, and the negative electrode active material may be metal magnesium, magnesium alloy, graphite, or the like. However, it is not limited to these materials, and conventional positive and negative electrode active materials of magnesium-ion batteries can be used. These positive and negative electrode active materials may be used individually in combination.

In the above batteries, the specific type of the separator is not specifically limited, and may be any separator material used in the existing batteries, such as polyethylene, polypropylene, polyvinylidene fluoride, and multilayer composite separator thereof, but not limited thereto.

The electrolytic solution is the electrolytic solution according to the first aspect.

In the above batteries, the positive electrode plate further includes a binder and a conductive agent. A positive electrode slurry containing the positive electrode active material, the binder, and the conductive agent is coated on a positive current collector and then dried to obtain the positive electrode plate. Similarly, a negative electrode slurry containing the negative electrode active material, a binder and a conductive agent is coated on a negative current collector, and then dried to obtain the negative electrode plate.

Further, the secondary batteries in the embodiments of the present application have a charging cut-off voltage of not less than 4.2V, and preferably operate in the range of 4.2V to 4.9V, more preferably in the range of 4.3V to 4.8V In a higher voltage state, the valence of the transition metal on the surface of the positive electrode material is higher, and the coulomb interaction between the transition metal and the nitrile groups in the multi-cyano compound is stronger, so that the additive can exert a corresponding protective effect to a greater extent.

EXAMPLES

The following specific examples of the present application merely illustrate the embodiments of the lithium-ion battery, but the present application is not limited thereto. The present application is described in detail in combination with the examples of the lithium-ion secondary battery. It should be understood that these examples are merely used to illustrate the present disclosure, but not intended to limit the scope of the present disclosure. The reagents, materials and instruments used in the following examples and comparative examples are commercially available, unless otherwise specified.

Preparation of Electrolytic Solution: a mixture of ethylene carbonate (EC), ethyl methyl carbonate (EMC) and diethyl carbonate (DEC) was used as solvent, in which a mass ratio of EC, EMC and DEC is 1:1:1. $LiPF_6$ was used as the lithium salt, and a total content of $LiPF_6$ is 12.5% of a total weight of the electrolyte. The additive is added to the composition of the electrolyte shown in Table 1 is added, in which the concentrations of the additive are ratios of the weight of the additive to the total weight of the electrolyte.

Preparation of Positive Electrode Plate: a positive electrode active material ($LiCoO_2$), a binder PVDF, and a conductive agent acetylene black were mixed in a mass ratio of 98:1:1, N-methylpyrrolidone was added, and the mixture was stirred under a vacuum to obtain stable and uniform positive electrode slurry. The positive electrode slurry was uniformly coated on an aluminum foil. The aluminum foil was dried at room temperature and transferred to a blast oven at 120° C. to be dried for 1 h, then subjected to cold-pressing and cutting to obtain a positive electrode plate.

Preparation of Negative Electrode Plate: a negative electrode active material (graphite), a conductive agent acetylene black, a thickener sodium carboxymethyl cellulose (CMC) solution, and a binder styrene-butadiene rubber emulsion were mixed according to a mass ratio of 97:1:1:1, then deionized water was added, and the mixture was stirred under a vacuum stirrer to obtain stable and uniform negative electrode slurry. The negative electrode slurry was evenly coated on a copper foil. The copper foil was dried at room temperature and transferred to a blast oven at 120° C. to be dried for 1 h, then subjected to cold-pressing and cutting to obtain a negative electrode plate.

Preparation of Battery: the positive electrode plate, the negative electrode plate, and a PP/PE/PP separator were wound to obtain a battery cell. After the battery cell was placed in a packaging case, the electrolytic solution was injected, and a battery was then obtained after sequential steps of sealing, standing-by, thermal and cold pressing, formation, exhausting, capacitance test, etc.

TABLE 1

Compositions of electrolytic solution and addition proportions thereof in examples and comparative examples

| No. | Solvent | Multi-cyano Compound | |
|---|---|---|---|
| | | Type | Concentration |
| Battery 1 | EC:EMC:DEC = 1:1:1 | A1 | 0.001% |
| Battery 2 | EC:EMC:DEC = 1:1:1 | A2 | 0.1% |
| Battery 3 | EC:EMC:DEC = 1:1:1 | A3 | 0.5% |
| Battery 4 | EC:EMC:DEC = 1:1:1 | A4 | 1.0% |
| Battery 5 | EC:EMC:DEC = 1:1:1 | A5 | 1.5% |
| Battery 6 | EC:EMC:DEC = 1:1:1 | A6 | 2.0% |
| Battery 7 | EC:EMC:DEC = 1:1:1 | A7 | 2.0% |
| Battery 8 | EC:EMC:DEC = 1:1:1 | A3 | 2.5% |
| Battery 9 | EC:EMC:DEC = 1:1:1 | A3 | 3.0% |
| Battery 10 | EC:EMC:DEC = 1:1:1 | A3 | 3.5% |
| Battery 11 | EC:EMC:DEC = 1:1:1 | A3 | 4.5% |
| Battery 12 | EC:EMC:DEC = 1:1:1 | A3 | 6% |
| Battery 13 | EC:EMC:DEC = 1:1:1 | A3 | 8% |
| Battery 14 | EC:EMC:DEC = 1:1:1 | A3 | 9% |
| Battery 15 | EC:EMC:DEC = 1:1:1 | A3 | 10.0% |
| Battery 16 | EC:EMC:DEC = 1:1:1 | A3 | 11.0% |
| Battery 17 | EC:EMC:DEC = 1:1:1 | — | — |
| Battery 18 | EC:EMC:DEC = 1:1:1 | hexanedinitrile | 2.0% |

Notes:
"—" denotes that the substance is absent.

Batteries 1 to 18 were tested as follows:

(1) Test of Cycle Performance of Wide Voltage Range of Lithium Ion Battery

At 25° C., in one charge/discharge cycle, the lithium ion battery was first charged at a constant current of 1 C to a voltage of 4.35V, further charged at a constant voltage of 4.35V to a current of 0.05 C, and then discharged at a constant current of 1 C to a voltage of 3.0V, a discharge capacitance is the discharge capacitance after the $1^{st}$ cycle. The lithium ion battery was subjected to a 500 charge/discharge cycles in the above manner, and the discharge capacitance after the $500^{th}$ cycle was detected.

Capacitance retention rate of lithium ion battery after 500 cycles (%)=(discharge capacitance of lithium ion battery after $500^{th}$ cycle/discharge capacitance of lithium ion battery after $1^{st}$ cycle)×100%.

(2) Test of Cycle Performance of Lithium Ion Battery Over a Wide Temperature Range At 45° C., in one charge/discharge cycle, the lithium ion battery was first charged at a constant current of 1 C to a voltage of 4.35V, further charged at a constant voltage of 4.35V to a current of 0.05 C, and then discharged at a constant current of 1 C to a voltage of 3.0V, a discharge capacitance is a discharge capacitance after the $1^{st}$ cycle. The lithium ion battery was subjected to a 200 charge/discharge cycles test in the above manner, and the discharge capacitance after the $200^{th}$ cycle was detected.

Capacitance retention rate of lithium ion battery after 200 cycles (%)=(discharge capacitance of lithium ion battery after $200^{th}$ cycle/discharge capacitance of lithium ion battery after $1^{st}$ cycle)×100%.

(3) Test of Storage Performance of Lithium Ion Battery Over Wide Temperature Range At 85° C., the lithium-ion battery was charged at a constant current of 0.5 C to a voltage of 4.35V, and then charged at a constant voltage of 4.35V to a current of 0.05 C, after that, the thickness of the lithium ion battery was tested and recorded as h0. Then, the lithium ion battery was placed in a 60° C. incubator and stored for 24 hours, then the thickness of the lithium ion battery was tested and recorded as h1.

Thickness expansion rate (%) of lithium ion battery after storage for 24 hours=[(h1−h0)/h0]×100%.

The experimental results are shown in Table 2.

TABLE 2

Experimental results of cycle capacitance retention rate and thickness expansion rate

| No. | Capacitance retention rate at 25° C. (4.35 V/500 cycles) | Capacitance retention rate at 45° C. (4.35 V/200 cycles) | Expansion rate at 85° C. (24 h) |
| --- | --- | --- | --- |
| Battery 1 | 88% | 86% | 39% |
| Battery 2 | 91% | 88% | 30% |
| Battery 3 | 94% | 91% | 16% |
| Battery 4 | 96% | 93% | 10% |
| Battery 5 | 97% | 95% | 7% |
| Battery 6 | 97% | 94% | 4% |
| Battery 7 | 99% | 97% | 3% |
| Battery 8 | 99% | 96% | 5% |
| Battery 9 | 97% | 96% | 3% |
| Battery 10 | 98% | 97% | 3% |
| Battery 11 | 96% | 95% | 4% |
| Battery 12 | 93% | 92% | 1% |
| Battery 13 | 90% | 88% | 3% |
| Battery 14 | 92% | 90% | 2% |
| Battery 15 | 90% | 86% | 1% |
| Battery 16 | 87% | 83% | 2% |
| Battery 17 | 83% | 75% | 67% |
| Battery 18 | 95% | 91% | 12% |

From the comparison results of the batteries 1 to 16 and the battery 17, it can be found that the multi-cyano compounds according to the present application can improve normal temperature and high temperature cycle performance and high temperature storage performance of the lithium ion battery under high voltage.

The multi-cyano compound of the present application has strong complexation with the transition metal on the surface of the positive electrode material, such that a protective film can be formed on the surface of the positive electrode material, which reduces the surface activity of the positive electrode material and suppresses side reactions such as decomposition of the electrolytic solution on the surface of the positive electrode material. Therefore, when the multi-cyano compound according to the present application is added to the electrolytic solution of the lithium ion battery, the cycle performance and storage performance of the battery under high voltage condition are improved to a certain extent, especially the high temperature storage performance is significantly improved. With an increase in the addition amount of the compound, the film-forming effect on the surface of the positive electrode material is better, so the improvement of the cycle performance and storage performance of the lithium-ion battery at room temperature and high temperature is more significant. When the mass percentage of the multi-cyano compound in the lithium ion battery electrolytic solution is increased to 1.5% to 3.5%, the cycle performance and storage performance of the lithium ion battery under normal temperature and high temperature can be effectively improved. If the mass percentage of the compound is further increased, the normal temperature and high temperature cycle performance of the lithium ion battery tends to decrease due to the great thickness and resistance of the film formed on the surface of the positive electrode material, while the high temperature storage performance approaches the optimal value.

Compared with the linear hexanedinitrile used in the battery 18, C=O group, S=O group and or P=S group contained in the multi-cyano compound of the present application can also be complexed with the metal elements on the surface of the positive electrode material, so that the adsorption sites are increased and the compound can be more stably adsorbed on the surface of the positive electrode material. Therefore, the multi-cyano compound of the present application has a better film-forming effect on the surface of the positive electrode material during the electrochemical reaction process, thereby significantly improving the cycle performance and high-temperature storage performance of the battery when compared with hexanedinitrile.

Based on the disclosure and teachings of the foregoing description, those skilled in the art may also make appropriate changes and modifications to the above embodiments.

Therefore, the present application is not limited to the specific embodiments disclosed and described above, and some modifications and changes to the present application should also fall within the protection scope of the claims of the present application. In addition, although some specific terms are used in this description, these terms are only for convenience of explanation and do not constitute a limitation to the present application.

What is claimed is:

1. An electrolytic solution, comprising an additive, the additive comprising a multi-cyano compound, wherein the multi-cyano compound is at least one of compounds represented by Formula I-2:

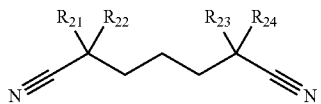

(I-2)

wherein $R_{21}$, $R_{22}$, $R_{23}$, and $R_{24}$ are each independently selected from the group consisting of a substituted or unsubstituted $C_2$-$C_8$ carbalkoxy, a substituted or unsubstituted $C_7$-$C_{16}$ aromatic ester group, a substituted or unsubstituted $C_2$-$C_8$ alkylcarbonyl, and a substituted or unsubstituted $C_7$-$C_{16}$ arylcarbonyl, at least one of $R_{21}$, $R_{22}$, $R_{23}$, and $R_{24}$ is a substituted or unsubstituted $C_7$-$C_{16}$ aromatic ester group, a substituted or unsubstituted $C_2$-$C_8$ alkylcarbonyl, or a substituted or unsubstituted $C_7$-$C_{16}$ arylcarbonyl, the substituent, if present, is selected from the group consisting of halogen, cyano, $C_1$-$C_6$ alkyl, and combinations thereof.

2. The electrolytic solution according to claim 1, wherein a mass percentage of the multi-cyano compound in the electrolytic solution is 0.001% to 10%.

3. The electrolytic solution according to claim 1, wherein a mass percentage of the multi-cyano compound in the electrolytic solution is 0.1% to 3.5%.

4. The electrolytic solution according to claim 1, wherein the multi-cyano compound is at least one of compounds represented by Formula I-2a:

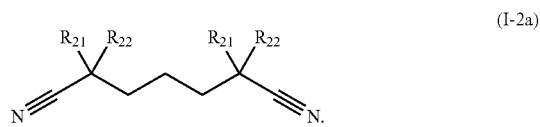

(I-2a)

5. The electrolytic solution according to claim 1, wherein the additive further comprises an additive A, and the additive A is selected from the group consisting of an unsaturated cyclic carbonate compound, a halogenated cyclic carbonate compound, a sulfate compound, a sulfite compounds, a sultone compound, a disulfonic acid compound, a nitrile compound, an aromatic compound, an isocyanate compound, a phosphazene compound, a cyclic anhydride compound, a phosphite compound, a phosphate compound, a borate compound, a carboxylate compound, and combinations thereof.

6. The electrolytic solution according to claim 5, wherein a mass percentage of the additive A in the electrolytic solution is 0.01% to 30%.

7. A battery, comprising a positive electrode plate, a negative electrode plate, a separator disposed between the positive electrode plate and the negative electrode plate, and an electrolytic solution, wherein the electrolytic solution is the electrolytic solution according to claim 1.

8. The battery according to claim 7, wherein the battery is a lithium ion battery, wherein a charging cut-off voltage of the battery is not lower than 4.2V.

* * * * *